(12) United States Patent
Martens et al.

(10) Patent No.: US 9,717,470 B2
(45) Date of Patent: Aug. 1, 2017

(54) ALIGNING SOURCE-GRATING-TO-PHASE-GRATING DISTANCE FOR MULTIPLE ORDER PHASE TUNING IN DIFFERENTIAL PHASE CONTRAST IMAGING

(71) Applicant: KONINKLIJKE PHILIPS N.V., Eindhoven (NL)

(72) Inventors: Gerhard Martens, Henstedt-Ulzburg (DE); Heiner Daerr, Hamburg (DE); Thomas Detlef Istel, Hamburg (DE); Ewald Roessl, Henstedt-Ulzburg (DE); Udo Van Stevendaal, Ahrensburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 238 days.

(21) Appl. No.: 14/421,008

(22) PCT Filed: Aug. 20, 2013

(86) PCT No.: PCT/IB2013/056748
§ 371 (c)(1),
(2) Date: Feb. 11, 2015

(87) PCT Pub. No.: WO2014/030115
PCT Pub. Date: Feb. 27, 2014

(65) Prior Publication Data
US 2015/0216499 A1  Aug. 6, 2015

Related U.S. Application Data

(60) Provisional application No. 61/684,869, filed on Aug. 20, 2012.

(51) Int. Cl.
*G01N 23/04* (2006.01)
*A61B 6/00* (2006.01)
*G01N 23/20* (2006.01)

(52) U.S. Cl.
CPC .............. *A61B 6/587* (2013.01); *A61B 6/484* (2013.01); *A61B 6/588* (2013.01); *A61B 6/589* (2013.01);
(Continued)

(58) Field of Classification Search
CPC ......... A61B 6/587; A61B 6/588; A61B 6/589; A61B 6/582; A61B 6/484; G01N 23/20025; G01N 23/20075; G01N 2223/643
(Continued)

(56) References Cited

U.S. PATENT DOCUMENTS

2011/0243300 A1  10/2011  Kaneko et al.
2012/0163537 A1   6/2012  Iwakiri et al.
2014/0270060 A1*  9/2014  Date ................. G01N 23/20075
                                                378/36

FOREIGN PATENT DOCUMENTS

WO  2008006470 A1  1/2008
WO  2013004574 A1  1/2013
WO  2013111050 A1  8/2013

* cited by examiner

*Primary Examiner* — Courtney Thomas

(57) ABSTRACT

An X-ray imaging method includes acquiring a differential phase contrast imaging X-ray scan with an X-ray imaging system having an X-ray source, an X-ray detector, and a grating arrangement having a source grating, a phase grating and an analyzer grating. The source grating is misaligned in respect to an interferometer such that moiré fringes are detectable in the plane of the detector. A translation signal is computed for translating the source grating for achieving a predetermined moiré pattern. The positioning of the source grating is adjusted in an X-ray projection direction based on the translation signal such that at least 2 pi of phase changes
(Continued)

are covered with the Moiré fringes over the width of the detector. And a further differential phase contrast imaging X-ray scan is acquired.

10 Claims, 4 Drawing Sheets

(52) U.S. Cl.
CPC . *G01N 23/20025* (2013.01); *G01N 23/20075* (2013.01); *A61B 6/582* (2013.01); *G01N 2223/643* (2013.01)

(58) Field of Classification Search
USPC .................................................. 378/62, 205
See application file for complete search history.

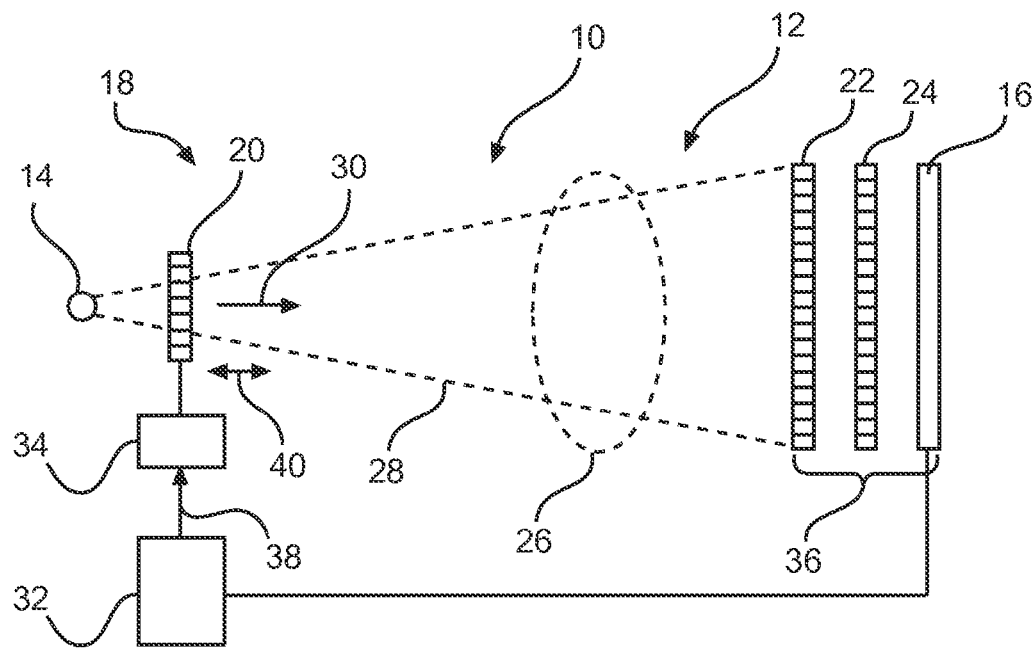
Fig.1
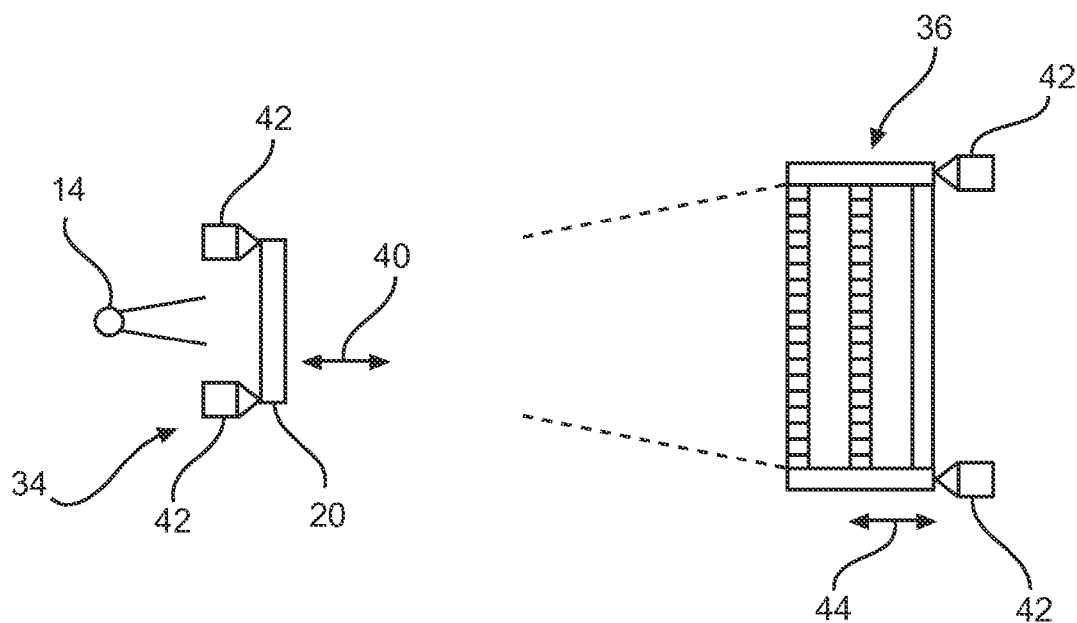
Fig.2a
Fig.2b

ALIGNING SOURCE-GRATING-TO-PHASE-GRATING DISTANCE FOR MULTIPLE ORDER PHASE TUNING IN DIFFERENTIAL PHASE CONTRAST IMAGING

CROSS-REFERENCE TO PRIOR APPLICATIONS

This application is the U.S. National Phase application under 35 U.S.C. §371 of International Application Serial No. PCT/IB2013/056748, filed on Aug. 20, 2013, which claims the benefit of U.S. application Ser. No. 61/684,869, filed on Aug. 20, 2012. These applications are hereby incorporated by reference herein.

FIELD OF THE INVENTION

The present invention relates to an X-ray imaging system for differential phase contrast imaging, to a method for handling misalignment in an X-ray imaging system for differential phase contrast imaging, to a computer program element and to a computer readable medium.

BACKGROUND OF THE INVENTION

Differential phase contrast imaging (DPCI) is an emerging technology that has a potential to improve the diagnostic value of X-ray imaging. For example, one application of this technology is mammography. In a DPCI system, a setup is used with three gratings between the X-ray source and the detector. For image acquisition, several X-ray images at different relative positions of two of the gratings are provided. Since the gratings have pitches in the order of a few micrometers only, there are rather tight requirements on the accuracy of the stepping device that performs the relative movement of the gratings, and also for alignment of the system. For larger objects, for example when investigating a breast, the virtual phase stepping is provided by using a scan of the object relative to the imaging system, including a virtual phase stepping parallel to this scan direction. For example, either the imaging system is moved relative to the sample/object, for example as application in mammography known from the Philips-owned company Sectra, Sweden, or the object/sample is moved with respect to a fixed imaging system, for example for security screening or baggage inspection. However, a requirement for all these setups is that across all detector lines, over the width D, i.e. parallel to the scan direction X, a phase shift of at least one interference fringe period of the interferometer, i.e. the analyser grating G2 and the phase grating G1, shows up. During the scan, each individual part of the object/sample successively passes the different detector lines, thus experiencing different phase states of the interferometer. The phase retrieval is then done by an evaluation of the detector line signal taken during the scan. As a requirement, the distance between the two gratings G1 and G2, i.e. the phase grating and the analyser grating, has to be adjusted precisely. Further, also the distance between the source grating G0 and the phase grating G1 has to be aligned precisely in all cases. However, it has been shown that tuning and stabilizing such an interferometer in hospital environments, for example, may consume unnecessary time and be cost-intensive.

SUMMARY OF THE INVENTION

Thus, there may be a need to provide a reduction for the pre-tuning and adjustment requirements for manufacture and maintenance in a differential phase contrast imaging system.

The object of the present invention is solved by the subject matter of the independent claims, wherein further embodiments are incorporated in the dependent claims.

It should be noted that the following described aspects of the invention apply also for the X-ray imaging system for differential phase contrast imaging, and for the method for handling misalignment in an X-ray imaging system for differential phase contrast imaging, as well as for the computer program element and the computer readable medium.

According to a first aspect of the present invention, an X-ray imaging system for differential phase contrast imaging is provided, comprising a differential phase contrast setup with an X-ray source and an X-ray detector, a grating arrangement and a moving arrangement for a relative movement between an object under examination and at least one of the gratings of the grating arrangement. The grating arrangement comprises a source grating, a phase grating, and an analyser grating. The source grating is arranged between the X-ray source and the phase grating, and the analyser grating is arranged between the phase grating and the detector. Further, a processing unit and a translation arrangement are provided. The translation arrangement is provided for translating the source grating. The phase grating, the analyser grating, and the detector are provided as a rigid interferometer unit, in which the phase grating and the analyser grating are mounted in parallel to each other. The source grating is misaligned in respect to the interferometer unit such that moiré fringes are detectable in the plane of the detector. The processing unit is configured to detect moiré patterns in signals provided by the detector upon X-ray radiation. The processing unit is further configured to compute a translation signal for translating the source grating for achieving a predetermined moiré pattern. The translation arrangement is configured to adjust the positioning of the source grating at least in the X-ray projection direction, based on the value of the translation signal.

The distance between the source grating and the phase grating is referred to as distance L, and the distance between the phase grating and the analyser grating is referred to as distance D. The imprecise adjustment of the distance D is compensated by the adjustment of the distance L. Therefore, a misalignment in the distance D, or a pre-set detuned D, can be compensated by an adjustment of L. Here, a precision in the sub-millimeter region is sufficient. The interferometer unit may also be referred to as detection unit. The misalignment may also comprise a deviation of the source grating and the interferometer unit in relation to each other.

According to an exemplary embodiment, the translation arrangement is configured to tilt the source grating.

According to an exemplary embodiment, the translation arrangement comprises at least one actuator for aligning the X-ray source unit and/or the X-ray detection unit.

According to an exemplary embodiment, the at least one actuator is provided as piezo actuator, and/or as motor-driven micrometer-screw. The motor-driven micrometer-screw can also be provided as micrometer-head. The at least one actuators provides a movement in the range of approximately 1 micrometer up to approximation 10 millimeters. The alignment accuracy of the actuator is approximately plus/minus 0.1 micrometer, according to an example.

According to an exemplary embodiment, the source grating is misaligned such that at least 2 pi of phase changes are covered with the moiré fringes over the width of the detector array.

According to an exemplary embodiment, a moving arrangement for a relative movement between an object under examination and at least one of the gratings is provided. For example, the moving arrangement is provided as a stepping arrangement for stepping at least one of the gratings of the interferometer unit in the respective grating plane.

Alternatively, an object support is provided and a relative movement between the object support and the differential phase contrast setup is provided, wherein the gratings are provided in a constant alignment to each other during a scan for at least one image acquisition. According to a first example, the object support is provided stationary, and the differential phase contrast setup is moved in a direction transverse to an X-ray direction. According to a second example, the differential phase contrast setup is provided stationary, and the object support is moved in a direction transverse to the X-ray direction. For example, in case of the moving arrangement as stepping arrangement, a stepping arrangement for stepping the source grating or the interferometer unit in the respective grating plane is provided. If one of the gratings of the interferometer unit is stepped, this can be provided with an accuracy of less than plus/minus 0.1 micrometer.

According to a second aspect of the present invention, a method for handling misalignment in an X-ray imaging system for differential phase contrast imaging is provided, comprising the following steps:

a) In a first step, at least a first differential phase contrast imaging X-ray scan is acquired with an X-ray imaging system for differential phase contrast imaging, comprising a differential phase contrast setup with an X-ray source, an X-ray detector, and a grating arrangement comprising a source grating, a phase grating, and an analyser grating. The source grating is misaligned in respect to the interferometer unit such that moiré fringes are detectable in the plane of the detector.

b) In a second step, moiré patterns in signals provided by the detector upon X-ray radiation are detected.

c) In a third step, a translation signal for translating the source grating for achieving a predetermined moiré pattern is computed.

d) In a fourth step, the positioning of the source grating is adjusted at least in an X-ray projection direction based on the translation signal.

e) In a fifth step, at least one further differential phase contrast imaging X-ray scan is acquired.

"Moiré fringes", also known as "moiré pattern", show up when superimposing two grids having nearly identical pitches either in the parallel as well as in an inclined configuration. For example, one grid in the phase contrast imaging set up is caused by the phase grating G1 as interference pattern of the x-ray beam, the other grid is the analyzer grid G2.

According to an exemplary embodiment, in step a), a plurality of first differential phase contrast imaging X-ray scans is acquired for different projection angles, and the scans are provided as a reference pattern for adjusting the position of the source grating for each projection angle individually.

According to an aspect of the present invention, the number of tuning and adjustment procedures is reduced to a minimum, and the precision that is necessary for the mechanical adjustment and demand on mechanical stability is shifted from the sub-micrometer region preferably into the sub-millimeter region or even higher. This is achieved, for example, by providing a movement of the source grating G0. Therefore, a compact rigid interferometer unit with the planes of the gratings G1 and G2 can be provided mounted in parallel with respect to each other. For example, the parallelism of the grid lines of G1 with respect to the G2 structures has to be around 0.1 millirad or better for typical grid pitch values encountered in low to medium energy X-ray interferometry. An occurring misalignment may be responsible for the appearance of moiré fringe components perpendicular to the grid structure. The number of moiré fringes parallel to the direction of the grid structures is dependent on the distance between G1 and G2 as well as on the distance between G0 and G1. More precisely, the number of moiré fringes is dependent on the quotient of the distance D to the distance L. Therefore, a misalignment in the distance D, or a pre-set detuned D, can be compensated by an adjustment of L. Here, a precision in the sub-millimeter region is sufficient. The total alignment that remains is the tuning of the distance between the grid G0, i.e. the source grating, and the interferometer as represented by the phase grating and the analyser grating. For example, this may be done by the aid of a linear translation stage, mounted to the rigid gantry that supports the X-ray tube, the interferometer and the detection unit. The distance L has to be tuned, for example, by the translation stage in such a way that at least one complete moiré fringe shows up across the width D of the detector. The number of moiré fringes may be further increased. However, the upper limit is reached by the number of detector lines per fringe falls below 4, for example.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings:

FIG. 1 shows an example of an X-ray imaging system in a schematic setup in a first example;

FIG. 2 shows a first further setup in FIG. 2A and a second further setup in FIG. 2B;

DETAILED DESCRIPTION OF EMBODIMENTS

Figure 3A:
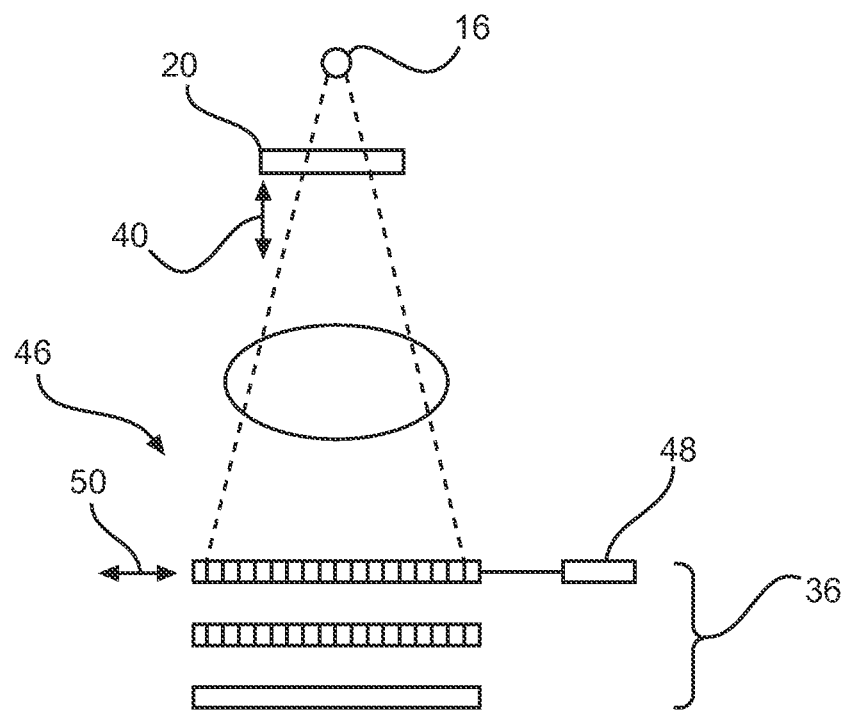
FIG. 3 shows further examples of an X-ray imaging system in relation with a first example of a moving arrangement in FIG. 3A, a second example for a moving arrangement in FIG. 3B, and a third example for a moving arrangement in FIG. 3C.

FIG. 1 shows an X-ray imaging system 10 for differential phase contrast imaging, comprising a differential phase contrast setup 12 with an X-ray source 14 and an X-ray detector 16. Further, a grating arrangement 18 is provided, comprising a source grating 20, a phase grating 22, and an analyser grating 24. The source grating is arranged between the X-ray source and the phase grating, and the analyser grating is arranged between the phase grating and the detector. Further, a moving arrangement for a relative movement between an object under examination and at least one of the gratings is provided (not further shown). A dotted oval structure 26 indicates an object, and an X-ray beam 28 in a fan-shaped formation is also indicated, together with an X-ray projecting direction 30. Further, a processing unit 32 is provided, and a translation arrangement 34 for translating the source grating. The phase grating, the analyser grating, and the detector are provided as a rigid interferometer unit 36, in which the phase grating and the analyser grating are mounted in parallel to each other.

The source grating is misaligned in respect to the interferometer unit 36 such that moiré fringes are detectable in the plane of the detector 16. The processing unit 32 is configured to detect such moiré patterns in signals provided by the detector 16 upon X-ray radiation. The processing unit 32 is further configured to compute a translation signal, indicated with an arrow 38, for translating the source grating 20 for achieving a predetermined moiré pattern. A double arrow 40 indicates the translation in the X-ray projection direction 30. The translation arrangement 34 is configured to adjust the positioning of the source grating 20 at least in the X-ray projection direction 30, based on the value of the translation signal.

For example, not further shown, the translation arrangement 34 is configured to tilt the source grating 20.

As indicated in FIG. 2, the translation arrangement 34 may comprise at least one actuator 42 for aligning the X-ray source unit and/or the X-ray detection unit, for example the source grating 20 can be moved by a number of piezo actuators or motor-driven micrometer-screws as the actuators 42. Of course, as shown in FIG. 2B, it is also possible to provide actuators 42 for moving the interferometer unit in relation to the source grating 20 and the X-ray source 14, as indicated with a second double arrow 44.

Figure 3B:
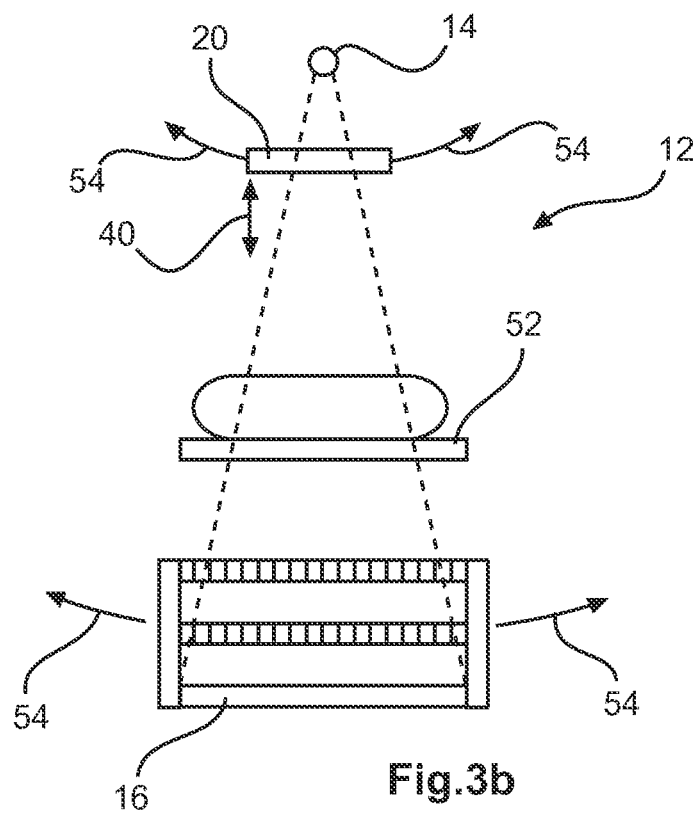
Figure 3C:
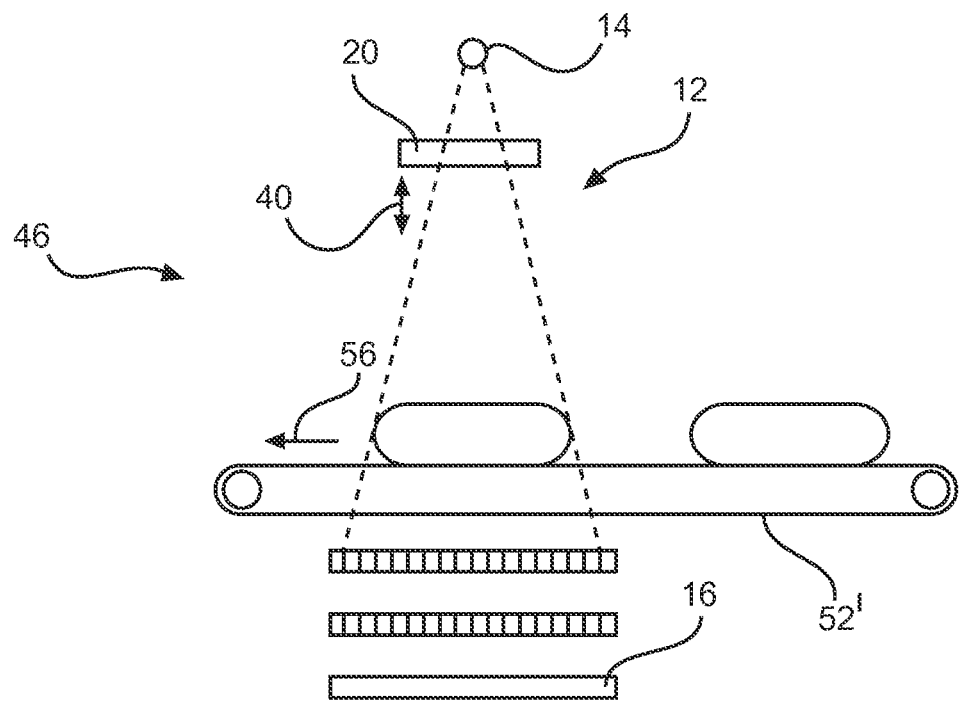

A moving arrangement 46 for a relative movement between an object under examination and at least one of the gratings is provided, as shown in FIGS. 3A, 3B, and 3C. As shown in FIG. 3A, the moving arrangement is provided as a stepping arrangement 48 for stepping, for example, the phase grating of the interferometer unit 36 in the respective grating plane, as indicated with a third double arrow 50. According to the example shown in FIG. 3A, the source grating 20 can also be moved, i.e. aligned, in the X-ray projection direction 30, and indicated with the above-mentioned double arrow 40.

As shown in FIG. 3B, the moving arrangement 46 can also be provided with an object support 52, and a relative movement between the object support and the differential phase contrast setup 12, wherein the gratings are provided in a constant alignment to each other during a scan for at least one image acquisition. The object support in FIG. 3B is provided stationary; the differential phase contrast setup is moved in a direction transverse to an X-ray direction, for example by a pivoting movement, indicated with pivoting indication arrows 54 around the location of the X-ray source 14. For example, such moving arrangement 46 can be provided for mammography. It must be noted that further key elements of a mammography investigation apparatus, such as breast compression paddles, are not further shown.

According to FIG. 3C, the moving arrangement 46 is provided with a stationary differential phase contrast setup, but a moving object support 52', for example a conveyer belt, for a movement in a direction transverse to the X-ray direction, as indicated with conveyer belt direction arrow 56, for example for luggage inspection.

Figure 4:
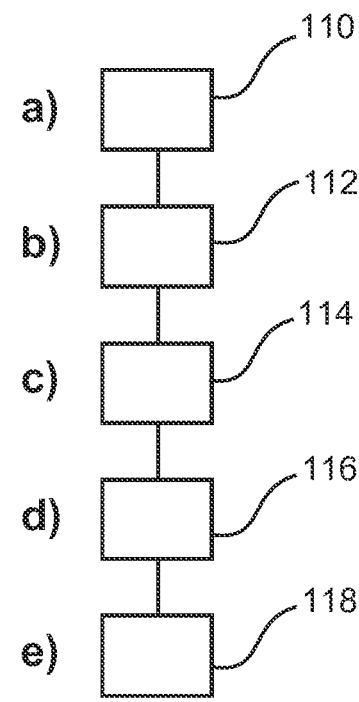
FIG. 4 shows basic steps of an example of a method for handling misalignment in an X-ray imaging system for differential phase contrast imaging.

FIG. 4 shows an example of a method 100 for handling misalignment in an X-ray imaging system for differential phase contrast imaging. In a first step 110, at least a first differential phase contrast imaging X-ray scan is acquired with an X-ray imaging system for differential phase contrast imaging, comprising a differential phase contrast setup with an X-ray source, an X-ray detector, and a grating arrangement comprising a source grating, a phase grating, and an analyser grating. The source grating is misaligned in respect to the interferometer unit such that moiré fringes are detectable in the plane of the detector. In a second step 112, moiré patterns are detected in signals provided by the detector upon X-ray radiation. In a third step 114, a translation signal is computed for translating the source grating for achieving a predetermined moiré pattern. In a fourth step 116, the positioning of the source grating is adjusted at least in an X-ray projection direction based on the translation signal. In a fifth step 118, at least one further differential phase contrast imaging X-ray scan is acquired. The first step 110 is also referred to step a), the second step 112 as step b), the third step 114 as step c), the fourth step 116 as step d), and the fifth step 118 as step e).

According to a further example, not shown, in step a), a plurality of first differential phase contrast imaging X-ray scans is acquired for different projection angles, and the scans are provided as a reference pattern for adjusting the position of the X-ray source grating for each projection angle individually.

Figure 5:
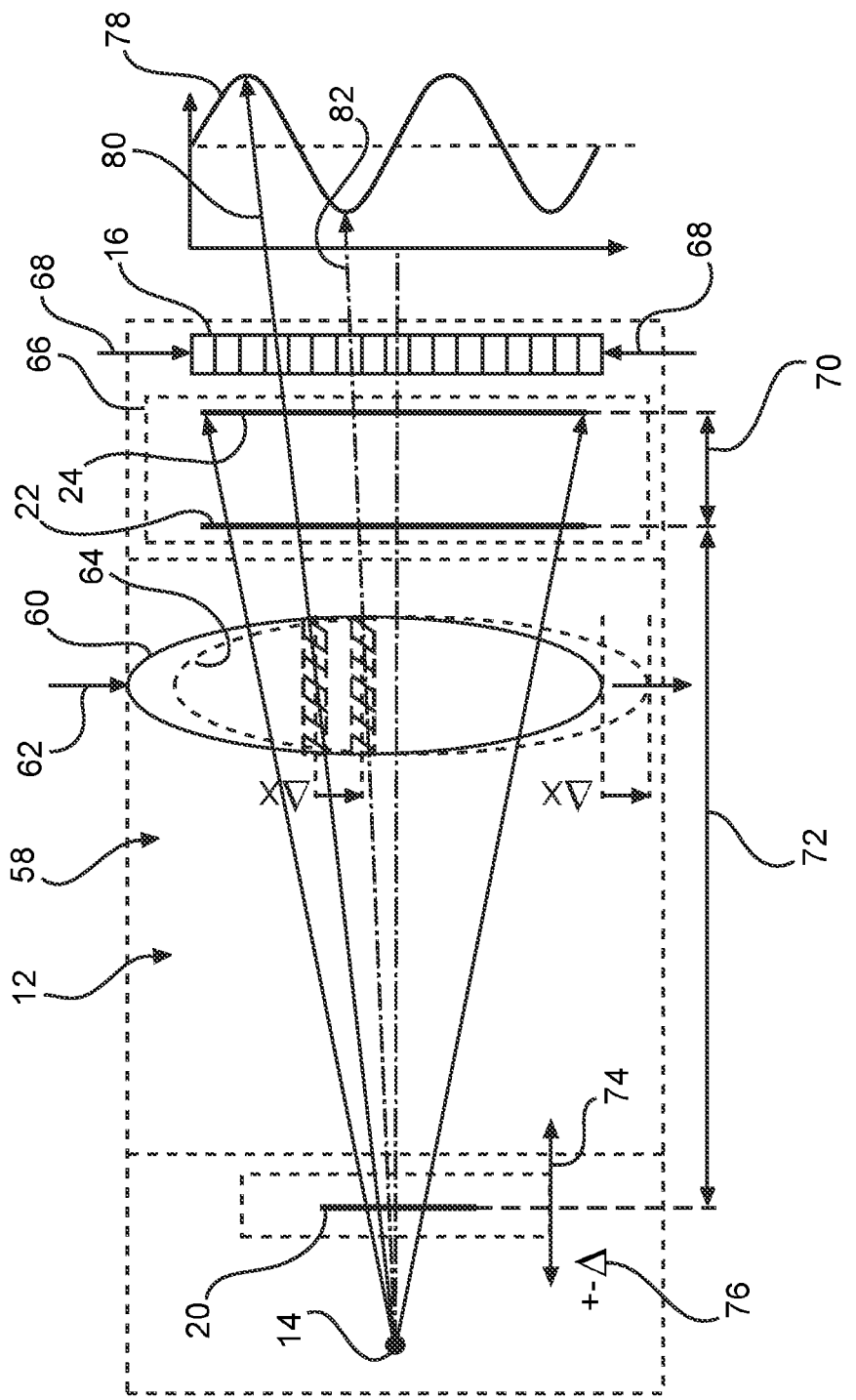
FIG. 5 shows a further setup of an example of an X-ray imaging system for differential phase contrast imaging.

FIG. 5 shows a further example of a differential phase contrast setup 12, with a first starting point representing the X-ray source 14, followed by the source grating 20. A space 58 for receiving an object 60, for example in a moving direction 62 is provided. The object 60 is shown for a first position with a straight line, and with a dotted pattern 64 for a second position upon being moved. Still further, the phase grating 22 and the analyser grating 24 are provided as a rigid unit, indicated with a dotted frame 66. Still further, a detector structure indicates the detector 16. The detector is characterized, among others, by the detector width, indicated with arrows 68. Further, the phase grating 22 and the analyser grating 24 are provided with a distance 70, and the phase grating 22 is provided in relation to the source grating 20 with a distance 72. The detector width 68 is also referred to as width D, the distance 70 between the phase grating 22 and the analyser grating 24 is also referred to as width d, and the distance between the source grating and the interferometer unit is referred to as distance L. A double arrow 74 indicates the alignment movement of the source grating 20 with a delta 76 of +/− delta L. Due to the provision of the grating arrangement and the scanning direction, a detector flux 78 can be measured, indicated with a curved graph. A first arrow 80 relates to a maximum point among the graph, and a dotted arrow 82 relates to a minimum point in the graph 78.

In an ideal system not employing phase contrast, each detector line would measure the same sonogram up no measurement noise. In a system as explained above, the different detector lines acquire different intensities due to the intentional misalignment in z between source and interferometer units. This misalignment causes the intensity measured by different detector lines to oscillate from one line to the next with a spatial period $\lambda$ inverse proportional to this mismatch, a phenomenon called moiré fringes. In order to assure a homogenous phase acquisition the number of detector elements N, the distance between two detectors D and the moiré period $\lambda$ have to obey the following relationship:

$$ND = n\lambda,$$

where n is the number of fringe period per entire detector array. The number of sampling points for the phase is thus given by $\lambda/D = N/n$ and should at least be at least 4, hence, for N=20 detector lines, n should at most be 5, typically 2.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application.

However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments.

Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An X-ray imaging system for differential phase contrast imaging, the system comprising:
    a differential phase contrast setup with:
        an X-ray source and an X-ray detector;
        a grating arrangement comprising a source grating, a phase grating and an analyzer grating, wherein the source grating is arranged between the X-ray source and the phase grating, and the analyzer grating is arranged between the phase grating and the detector; and
        a moving arrangement for a relative movement between an object under examination and at least one of the source grating, phase grating, and analyzer grating;
    a processor; and
    a translation arrangement for translating the source grating; wherein:
    the phase grating, the analyzer grating and the detector are provided as a rigid interferometer, in which the phase grating and the analyzer grating are mounted in parallel to each other;
    the source grating is misaligned in respect to the interferometer such that moiré fringes are detectable in the plane of the detector;
    the processor is configured to detect moiré patterns in signals provided by the detector upon X-ray radiation; and
    the processor is further configured to compute a translation signal for translating the source grating for achieving a predetermined moiré pattern; and
    the translation arrangement is configured to adjust the positioning of the source grating at least in the X-ray projection direction, based on the value of the translation signal for misaligning the source grating such that at least 2 pi of phase changes are covered with the moiré fringes over the width of the detector.

2. The X-ray imaging system according to claim 1, wherein the translation arrangement is configured to tilt the source grating.

3. The X-ray imaging system according to claim 1, wherein the translation arrangement comprises at least one actuator for aligning the X-ray source or the X-ray detector.

4. The X-ray imaging system according to claim 1, wherein the at least one actuator is provided as a piezo actuator or a motor-driven micrometer-screw that provides a movement in the range of approximately 1 micrometer up to approximately 10 micrometer.

5. The X-ray imaging system according to claim 1, wherein:
    i) the moving arrangement is provided as a stepping arrangement for stepping at least one of the source grating, phase grating, and analyzer grating in a respective grating plane; or
    ii) an object support is provided a relative movement between the object support and the differential phase contrast setup; wherein the source grating, phase grating, and analyzer grating are provided in a constant alignment to each other during a scan for at least one image acquisition; wherein:
  ii1) the object support is provided stationary; and the differential phase contrast setup is moved in a direction transverse to an X-ray direction; or
  ii2) the differential phase contrast setup is provided stationary; and the object support is moved in the direction transverse to the X-ray direction.

6. A method for handling misalignment in an X-ray imaging system for differential phase contrast imaging, the method comprising:
  a) acquiring at least a differential phase contrast imaging X-ray scan with the X-ray imaging system, which comprises a differential phase contrast setup with an X-ray source, an X-ray detector, and a grating arrangement comprising a source grating, a phase grating and an analyzer grating; wherein the source grating is misaligned in respect to an interferometer such that moiré fringes are detectable in the plane of the detector;
  b) detecting moiré patterns in signals provided by the detector upon X-ray radiation;
  c) computing a translation signal for translating the source grating for achieving a predetermined moiré pattern; and
  d) adjusting the positioning of the source grating at least in an X-ray projection direction based on the translation signal for misaligning the source grating such that at least 2 pi of phase changes are covered with the moiré fringes over the width of the detector;
  e) acquiring at least one further differential phase contrast imaging X-ray scan.

7. A non-transitory computer-readable medium having stored therein a computer program element that when executed by a processor is adapted to perform the method of claim 6.

8. The method of claim 6, wherein a translation arrangement adjusts the positioning of the source grating in the X-ray projection direction and is configured to tilt the source grating.

9. The method of claim 6, wherein a translation arrangement adjusts the positioning of the source grating in the X-ray projection direction and comprises an actuator for aligning the X-ray source or the X-ray detector.

10. The method of claim 9, wherein the actuator is a piezo actuator or a motor-driven micrometer-screw that provides a movement in the range of approximately 1 micrometer up to approximately 10 micrometer.

* * * * *